(12) United States Patent
Hsieh et al.

(10) Patent No.: US 10,092,612 B2
(45) Date of Patent: Oct. 9, 2018

(54) ***GARCINIA MANGOSTANA* COMPOSITION, MEDICATION AND HEALTH FOOD INCLUDING THE SAME**

(71) Applicant: LORD DUKE BIOTECHNOLOGY CORPORATION, Taipei (TW)

(72) Inventors: Hsiu-Mei Hsieh, Taipei (TW); Hui-Chen Huang, Taipei (TW); Yin-Jun Chen, Taipei (TW)

(73) Assignee: LORD DUKE BIOTECHNOLOGY CORPORATION, Taipei (TW)

( * ) Notice: Subject to any disclaimer, the term of this patent is extended or adjusted under 35 U.S.C. 154(b) by 272 days.

(21) Appl. No.: 15/246,940

(22) Filed: Aug. 25, 2016

(65) Prior Publication Data

US 2016/0361371 A1    Dec. 15, 2016

(30) Foreign Application Priority Data

Feb. 2, 2016 (TW) .............................. 105103381 A (51) Int. Cl.
| | |
|---|---|
| *A61K 36/00* | (2006.01) |
| *A61K 36/38* | (2006.01) |
| *A61K 36/258* | (2006.01) |
| *A23L 33/105* | (2016.01) |
| *A61K 9/00* | (2006.01) |

(52) U.S. Cl.
CPC ............ *A61K 36/38* (2013.01); *A23L 33/105* (2016.08); *A61K 36/258* (2013.01); *A23V 2002/00* (2013.01); *A61K 9/0019* (2013.01); *A61K 2236/10* (2013.01); *A61K 2236/15* (2013.01); *A61K 2236/331* (2013.01)

(58) Field of Classification Search
CPC ....................................................... A61K 36/00
USPC .......................................................... 424/725
See application file for complete search history.

(56) References Cited

PUBLICATIONS

"American Ginseng (*Panax quinquefolius*)", http://fuyu.com.tw/ContentPrint.asp?ContentId=2223, Oct 7, 2014, 2 pages.
Ping-Hung Chen, "Garcinia mangostana", http://plantsmedicine.bloqspot.tw/2011/12/garcinia-mangostana.html, Dec. 5, 2011, 2 pages.

*Primary Examiner* — Michael V Meller
(74) *Attorney, Agent, or Firm* — Muncy, Geissler, Olds & Lowe, P.C.

(57) ABSTRACT

A *Garcinia mangostana* composition, a medication and a health food including the same for enhancing learning ability and memory of a patient with Alzheimer's disease are provided. The *Garcinia mangostana* composition includes *G. mangostana* and *P. quinquefolius*. The net weight ratio of the *G. mangostana* to the *P. quinquefolius* ranges from 4:1 to 1:16. A total of 4.5 to 35 mg of *G. mangostana* is per kilogram bodyweight applied, and 9 to 70 mg of *P. quinquefolius* per kilogram bodyweight is applied. The *G. mangostana* composition is capable of reducing the neuronal cell death and increasing the neurite length of the subjects with Alzheimer's disease, as well as improving the short term memory and the long term memory of the test subjects.

1 Claim, 4 Drawing Sheets

GARCINIA MANGOSTANA COMPOSITION, MEDICATION AND HEALTH FOOD INCLUDING THE SAME

CROSS-REFERENCE TO RELATED APPLICATION

This application claims priority from Taiwan Patent Application No. 105103381, filed on Feb. 2, 2016, in the Taiwan Intellectual Property Office, the content of which is hereby incorporated by reference in its entirety for all purposes.

BACKGROUND OF THE INVENTION

1. Field of the Invention

The present invention is related to *Garcinia mangostana* (*G. mangostana*) composition and the medication and health food including the same. Specifically, the exemplary embodiments of the present invention relate to *G. mangostana* composition and the medication and health food including the same for enhancing the learning ability and memory of patient with Alzheimer's disease (AD).

2. Description of the Related Art

Being the most common neurodegenerative disease, senile dementia is actually a general term for various similar neurodegenerative diseases, wherein the most common type of senile dementia is the AD. Currently, there are 48 million people diagnosed with AD worldwide, and with the onset of population aging, there will be an increment of 4.6 million cases annually. The World Health Organization (WHO) estimates that there will be 80 million patients with AD by 2040. Alzheimer's disease is a chronic neurological disorder that progresses slowly but deteriorates over time. The most common symptom during the onset of AD is the loss of short term memory. Then, as the disease progresses, the symptoms may include: delirium, short temper, aggression, aphasia, disorientation, emotional instability, loss of motivation of life, loss of long term memory, having problems with self-care and behavioral issues. The rate of progression varies from one patient to another, making it difficult to estimate the prognosis for patients. However, generally speaking, the average life expectancy is three to nine years upon confirmed diagnosis.

The cause of AD is not yet fully understood. So far, it is found that the neurons inside the patients' brain tend to form plaques and Neurofibrillary Tangles (NFTs), and the nucleus basalis of Meynert in the brain tends to degenerate, as well as the synthesis of neurotransmitter acetylcholine tends to reduce. The NFTs refer to the tangled nerve cell bodies found during the pathological anatomy of the patient's brain. The cellular structure is severely deformed, and the deformed neurons stack together to form a clump. It is discovered that the formation of NFTs is associated with the hyperphosphorylation of Tau protein, which causes the tau protein to accumulate and induce cytotoxicity, thereby damaging the neurons directly or indirectly.

Although various drugs against AD have been developed, the biggest obstacle to curing AD is that there is no single effective treatment for such disease. Clinically, the usual treatment of small-molecule compounds only improves the symptoms, instead of stopping the progression of the disease. Therefore, there is an imperative need to develop a method capable of mitigating the memory loss due to AD, or even stopping the progression of AD.

SUMMARY OF THE INVENTION

In light of the aforementioned technical issues, an objective of the present invention is to provide a composition and the medication and health food including the composition to suppress the progression of Alzheimer's disease (AD). Especially, the objective of this invention is to provide a composition of *Garcinia mangostana* (*G. mangostana*) and *Panax quinquefolius* (*P. quinquefolius*), as well as to provide the medication and health food including the composition to suppress the progression of AD in vivo, so as to effectively enhance the learning ability and memory in vivo.

In order to achieve the aforementioned objective, the present invention provides a composition for enhancing learning ability and memory of a patient with AD, including *G. mangostana* and *P. quinquefolius*. The net weight ratio of the *G. mangostana* to the *P. quinquefolius* may range from 4:1 to 1:16. Wherein, 4.5 to 35 mg of *G. mangostana* may be administered per kilogram bodyweight, and 9 to 70 mg of *P. quinquefolius* may be administered per kilogram bodyweight.

Preferably, the *G. mangostana* may be obtained from fresh *G. mangostana*, dried *G. mangostana*, powdered *G. mangostana*, frozen *G. mangostana* or any combination thereof.

Preferably, the *P. quinquefolius* may be obtained from fresh *P. quinquefolius*, dried *P. quinquefolius*, powdered *P. quinquefolius*, frozen *P. quinquefolius* or any combination thereof.

Preferably, the *G. mangostana* may be extracted with water, oil, polar solvent, non-polar solvent or a combination thereof.

Preferably, the *P. quinquefolius* may be extracted with water, oil, polar solvent, non-polar solvent or a combination thereof.

Preferably, the *G. mangostana* composition may be in powdered-form, tablet-form or liquid-form.

In order to achieve the aforementioned objective, the present invention further provides a medication composition for enhancing learning ability and memory of a patient with AD, including a *G. mangostana* composition. Wherein, the *G. mangostana* composition may include *G. mangostana* and *P. quinquefolius*.

Preferably, the net weight ratio of the *G. mangostana* to the *P. quinquefolius* may range from 4:1 to 1:16; 4.5 to 35 mg of *G. mangostana* may be applied per kilogram bodyweight, and 9 to 70 mg of *P. quinquefolius* may be applied per kilogram bodyweight.

Preferably, the *G. mangostana* composition is capable of increasing the length of neurite and increases the survivability of neurons.

Preferably, the route of administration of the medication may include oral administration, intramuscular injection, subcutaneous injection or administration to the brain.

In order to achieve the aforementioned objective, the present invention further provides a health food composition for enhancing learning ability and memory of a patient with AD, including a *G. mangostana* composition. Wherein, the *G. mangostana* composition may include *G. mangostana* and *P. quinquefolius*.

Preferably, the net weight ratio of the *G. mangostana* to the *P. quinquefolius* may range from 4:1 to 1:16; 4.5 to 35 mg of *G. mangostana* may be applied per kilogram bodyweight, and 9 to 70 mg of *P. quinquefolius* may be applied per kilogram bodyweight.

Preferably, the *G. mangostana* composition is capable of increasing the length of neurite and increases the survivability of neurons.

Preferably, the route of administration of the health food may include oral administration, intramuscular injection, subcutaneous injection or administration to the brain.

The composition of the present invention can be used for enhancing learning ability and memory of a patient with AD. Wherein, the composition formed with the combination of *G. mangostana* and *P. quinquefolius* may possess the benefits listed below:

(1) By using the combination of *G. mangostana* and *P. quinquefolius*, the *G. mangostana* composition of the present invention is capable of both reducing the neuronal cell death and increasing the neurite length of the patients with AD, in contrast to using *G. mangostana* or *P. quinquefolius* alone.

(2) In contrast to using *G. mangostana* or *P. quinquefolius* alone, the *G. mangostana* composition of the present invention is capable of improving the short term memory and the long term memory of the test subjects dramatically.

(3) By using the combination of *G. mangostana* and *P. quinquefolius*, the *G. mangostana* composition of the present invention is capable of improving the learning ability of the test subjects dramatically, in contrast to using *G. mangostana* or *P. quinquefolius* alone.

BRIEF DESCRIPTION OF THE DRAWINGS

The exemplary embodiment(s) of the present invention will be understood more fully from the detailed description given below and from the accompanying drawings of various embodiments of the invention, which, however, should not be taken to limit the invention to the specific embodiments, but are for explanation and understanding only.

FIGS. 1A and 1B show the test results of in vitro primary culture of hippocampal neurons from laboratory mice after being treated respectively with *G. mangostana* (noted as GM in FIGs) and/or *P. quinquefolius* (noted as PQ in FIGs). FIG. 1B shows the neurite lengths of the primary hippocampal neurons of the laboratory mice after treatment. "*" indicates comparison with control group (treated with the solvent DMSO), whereas "#" indicates comparison with the control group treated with WT/GFX. "&" indicates respective comparisons with twice the amount of single ingredient. (# and &, $p<0.05$; **, ## and &&, $p<0.01$; ### and &&&, $p<0.001$).

FIGS. 2A and 2B illustrate the procedure of the animal testing and the experiment results for Y maze test. FIG. 2B is the bar chart showing the spontaneous alternation rate of the mice. "*" indicates the comparison with control group (saline solution/saline solution); "#" indicates the comparison with streptozotocin (STZ) group (STZ/saline solution). (* and #, $p<0.05$; ###, $p<0.001$).

FIGS. 3A-3D show the analyzed results of the Morris water maze (MWM) test performed during days 28-34 (after treated with *G. mangostana* and/or *P. quinquefolius* for 22-28 days). FIG. 3C shows the analyzed results on day 33. FIG. 3D illustrates the frequency of the mice crossing the platform quadrant on day 34. "*" indicates the comparison with control group (saline solution/saline solution); "#" indicates the comparison with STZ group (STZ/saline solution). (* and #, $p<0.05$; ##, $p<0.01$).

DESCRIPTION OF THE PREFERRED EMBODIMENTS

Those of ordinary skilled in the art will realize that the following detailed description of the exemplary embodiment(s) is illustrative only and is not intended to be in any way limiting. Other embodiments will readily suggest themselves to such skilled persons having the benefit of this disclosure. Reference will now be made in detail to implementations of the exemplary embodiment(s) as illustrated in the accompanying drawings. The same reference indicators will be used throughout the drawings and the following detailed description to refer to the same or like parts.

Definition

When the term "approximately" or "about" is used in conjunction with a measurable variable, it refers to the indicated value of the variable and the maximum value taken from the set of all values that fall within the experimental error of that indicated value, e.g. 95% confidence interval of the mean, or the set of all values that fall within 10% of the indicated value of the variable.

The term "administration" refers to the act of putting substance into the body of a test subject, for instance the *G. mangostana* and *P. quinquefolius* composition is administered to a subject by the route of administration including at least: oral and non-oral, e.g. subcutaneous, intramuscular, transdermal, intradermal, intraperitoneal, intravitreal, intravenous injections and administration to the brain.

The term "subject" refers to any mammal that requires or is suspected of requiring the composition of the present invention, including primates, rodents, pets, laboratory animals and domesticated wild animals. The non-limiting examples of the subjects may include: monkeys, humans, pigs, bovines, sheep, goats, equids, mice, rats, guinea pigs, hamsters, rabbits, felines and canines. Preferably, the subject is a mouse or human.

The term "excipient" refers to any ingredient in the *G. mangostana* composition that does not belong to the active ingredients of the *G. mangostana* and *P. quinquefolius*.

Ingredients and Methodology

Laboratory Animals

Mice: breed C57BL/6J, pregnant female mice and male mice that were 8 weeks old, acquired from National Laboratory Animal Center (NLAC) in Taiwan. The mouse room conditions were: temperature of 20-25° C., relative humidity of 60%, and 12 hours of light/dark cycle. All experiments were conducted during the time from 7 a.m. to 7 p.m. All experiment procedures fully complied with the rules and regulations stipulated by the Institutional Animal Care and Use Committee (IACUC) of National Taiwan Normal University (NTNU).

Primary Culture of Hippocampal Neurons from Mouse and Handling of Drugs

The previous research done by Seibenhener and Wooten in 2012 was modified to establish the method to grow the primary culture of hippocampal neurons from mice. The pregnant female mouse from breed C57BL/6J was sacrificed by cervical dislocation, and the 16-18 days old embryo was taken out. The hippocampal issue thereof was removed and is digested with 0.05% trypsin for 15 minutes under the temperature of 37° C. $3 \times 10^4$ cells were transferred to each well of the 24-well or 6-well plates coated with Poly-L-lysine (100 µg/ml). Ingredient of the growth medium: Neurobasal® Medium (Gibco™; ThermoFisher Scientific, USA), added with 2% B-27® Supplement (Gibco™; ThermoFisher Scientific, USA), 0.5 mM glutamine (Gibco™; ThermoFisher Scientific, USA), 25 µM glutamate (Sigma-Aldrich, USA), 20 unit/ml of penicillin/streptomycin (Gibco™; ThermoFisher Scientific, USA), 1 mM of 4-(2-hydroxyethyl)-1-piperazineethanesulfonic acid (HEPES) (Sigma-Aldrich), and 1% heat inactivated Donor Horse serum (Gibco™; ThermoFisher Scientific, USA). The primary culture of mouse hippocampal neurons was incubated in the incubator under temperature of 37° C. and carbon dioxide concentration of 5%. On the day 1, 4 and 7 of the incubation, half of the growth medium was replaced with new growth medium without the horse serum. On day 4 and day 7 of the incubation, 2 µM of cytosine arabinoside (Sigma-Aldrich) was added, so as to increase the purity of the neurons by reducing the number of the astrocytes. On day 9 of the incubation, the neurons received different doses of *G. mangostana* and *P. quinquefolius*, as well as 10 nM of Wortmannin (WT)/GF-109203X (GFX) (will be abbreviated as WT/GFX) or DMSO, and was incubated for another 1 hour.

Immunofluorescence

For the primary culture of the hippocampal neurons from the mouse, 1 hour after being treated with 10 nM WT/GFX or the solvent DMSO thereof, the cells were fixed with 4% paraformaldehyde (Sigma-Aldrich) for 30 minutes. Then the cells were washed three times with PBST, 10 minutes once, in order to remove residual paraformaldehyde. Then fetal bovine serum (FBS) of 10% was applied to destroy the nonspecific reaction thereof for 2 hours. After that, anti-NeuN primary antibody (1:1000; Millipore, USA) and anti-MAP2 primary antibody (1:1000; Millipore, USA) were added, and allowed to react for 16 hours at 4° C., and then reacted with the secondary antibodies for 2 hours at 37° C. Finally, after staining the neuronal nuclei with 4',6-diamino-2-phenylindole (DAPI, Sigma-Aldrich, USA), the neurons and various values such as the neurites length were measured using high throughput microscopy system and MetaXpress® analysis software (Molecular Devices, USA).

Preparation for *G. mangostana* Composition

The inventor froze dried the entire fruits of *G. mangostana* and *P. quinquefolius* respectively to dehydrate them, and then grounded the dehydrated *G. mangostana* and *P. quinquefolius* into powder. The *G. mangostana* may be derived from, but is not limited to, fresh *G. mangostana*, dried *G. mangostana*, powdered *G. mangostana*, frozen *G. mangostana* or any combination thereof. Preferably, the *G. mangostana* of the present invention was derived from fresh *G. mangostana*. The *P. quinquefolius* may be derived from, but is not limited to, fresh *P. quinquefolius*, dried *P. quinquefolius*, powdered *P. quinquefolius*, frozen *P. quinquefolius* or any combination thereof. Preferably, the *P. quinquefolius* of the present invention was derived from fresh *P. quinquefolius*. Subsequently, the powdered *G. mangostana* and *P. quinquefolius* were mixed in the ratio that ranges from 4:1 to 1:16, preferably in the ratio of 1:2.

On the other hand, the *G. mangostana* composition of the present invention may further include *G. mangostana* extract and *P. quinquefolius* extract. The *G. mangostana* extract and *P. quinquefolius* extract may be obtained by extraction methods that are known in the art. The extraction method may be steam distillation, extraction with non-polar solvents, extraction with polar solvents, or extraction with carbon dioxide, but not limited thereto. The non-polar solvents applied in the extraction process may include petroleum ether, methylbenzene, etc., whereas the polar solvents applied in the extraction process may include ethanol, propanol, etc. The *G. mangostana* extract and *P. quinquefolius* extract of the present invention are obtained by extraction with water, so as to avoid the presence of residual solvents that are harmful to human body, but the present invention is not limited thereto. Besides, the net weight ratio of the *G. mangostana* extract to the *P. quinquefolius* extract may range from 4:1 to 1:16, preferably 1:2

In Vivo Experiment and the Drugs Administration

The cerebral lateral ventricles of the mice were injected with 3 µl (3 mg/kg) of STZ by stereotactic surgery, so as to establish non-transgenic mouse model (i.c.v.-STZ) with sporadic AD. Wherein, STZ was a medication that destroys insulin producing β cells as well as causes insulin resistance. The mice with AD were divided into five groups, 16 mice per group. The mice with AD in each group were respectively administered with *G. mangostana* (GM) and/or *P. quinquefolius* (PQ), and the results were observed. The drugs administration lasted for four weeks, and a series of assessments on the mice's behavior were performed. Finally, the mice were sacrificed for pathological analysis. The drugs administered to the five groups are listed in Table 1 below:

TABLE 1

| Group | Intracerebroventricular Injection (icv) | Per os (Once A Day) |
|---|---|---|
| 1 (Control Group) | Saline Solution | Saline Solution |
| 2 | STZ | Saline Solution |
| 3 | STZ | GM (40 mg/kg) |
| 4 | STZ | PQ (80 mg/kg) |
| 5 | STZ | GM (40 mg/kg) and PQ (80 mg/kg) |

Behavioral Assessment: Y Maze Test

The Y maze behavioral test module having three arms, with 35 cm in length, 5 cm in width and 20 cm in height, is made from white acrylic. Taking advantage of the explorative nature of mouse, the short-term spatial memory of the mouse was tested with the Y maze. The mouse was placed at the center of the Y maze's three arms, and then the mouse was given 8 minutes to freely explore around. When all four limbs of the mouse stepped into one of the three arms, it would be counted as one entry. Wherein, the rate of spontaneous alternation=the number of entries into three arms without repetition*100/(total number of entries into each arm−2).

Behavioral Assessment: Morris Water Maze Test

Morris Water Maze (MWM) test refers to the test in which the spatial learning ability and memory of the mouse are tested by placing a platform at certain location of a large pool. Since mouse dislikes staying in the water and requires a lot of stamina to swim, it is the basic instinct of the mouse to search for resting place (the platform) in the water. The action of searching for platform involves complex memory process of the brain, including (1) collecting visual information related to spatial positioning, such as geometrical information of square, circle, triangle, etc., and (2) the functions of processing, organizing, memorizing, consolidating and recalling the information. The pool was filled with white toxic-free poster paint, such that the non-transparent liquid therein can hide the platform, and the mice would be unable to locate the platform in advance. The mouse was placed in the pool filled with the poster paint so that the mouse will search for the platform that is submerged in the liquid and fixed at certain quadrant of the pool. The training session was divided into several phases: 1. Exploration Phase: the mouse was placed in the liquid for 1 minute, if the mouse was unable to locate the platform in the given time, the mouse was retrieved and placed on the platform for 20 seconds. Then the mouse was allowed to rest in a dry area to wait for the consecutive experiment. 2. Assessment Phase: the mouse was released into the water maze from four specific locations to test whether the mouse is able to locate the platform successfully. The mice were trained four times a day for four days, i.e. each mouse had 16 training sessions. After four days of training, the learning ability acquired by the mouse was measured at the testing trial. The swimming velocity was also determined at this trial. 24 hours after the testing session the platform was removed. This time, the mouse was allowed to swim freely in the pool for 1 minute, in order to test whether the mouse was still able to remember the location of the platform (long-term spatial memory test). The path of swimming was recorded with CCD and subsequently analyzed with the video tracking system EthoVision-XT.

Statistics

One-way ANOVA and post hoc analysis, i.e. Fisher's least significant difference (LSD) were performed to all data using SPSS version 15.0.

Embodiments

In order to test whether the combination of *G. mangostana* (GM) and *P. quinquefoliu* (PQ) has any efficacy to alleviate AD, living tissue and animals were subjected to in vitro and in vivo tests.

In Vitro Test

The Simulated AD Cells Treated with WT/GFX

In order to understand the effect of *G. mangostana* and *P. quinquefoliu* on neurons with AD, first and foremost, the half maximal inhibitory concentrations ($IC_{50}$) of *G. mangostana* and *P. quinquefoliu* were measured using neuroblastoma cell line SH-SY5Y, which were found to be 10.0 mg/ml and 20.0 mg/ml respectively. The primary hippocampal neurons from mouse were cultured in vitro and then treated with WT/GFX on day 9 of the culturing process, such that Tau protein was hyperphosphorylated to simulate the state of AD in the cells. Then the cultured cells were treated with different doses of *G. mangostana* ranging from $IC_{50}/2000$ to $IC_{50}/250$, i.e. 5-40 μg/ml, and/or treated with different doses of *P. quinquefoliu* ranging from $IC_{50}/2000$ to $IC_{50}/250$, i.e. 10-80 μg/ml. The inventor combined different doses of *G. mangostana* and *P. quinquefoliu* amounting to different fractions of their respective $IC_{50}$, and applies the combination to the mouse's primary hippocampal neurons that were cultured in vitro for testing. It was found that as long as *G. mangostana* is used in conjunction with *P. quinquefoliu*, regardless of the ratio of *G. mangostana* to *P. quinquefoliu*, the effect of the treatment is better than that of single ingredient. The ratio of GM to *P. quinquefoliu* may be 4:1 (40 μg/ml:10 μg/ml), 1:1 (40 μg/ml:40 μg/ml), 2:1 (40 μg/ml:20 μg/ml), 1:1 (10 μg/m1:10 μg/ml), 1:2, etc., but not limited thereto. Among the combinations with different ratios, the inventor further applies the combination of *G. mangostana* and *P. quinquefoliu* in the ratio of 1:2 to the mouse's primary hippocampal neurons for testing, the dosage of the combination is represented by Table 2 below:

TABLE 2

Concentration of *G. mangostana* and *P. quinquefoliu* Applied for In Vitro Experiment

| Dosage in Terms of $IC_{50}$ | *G. mangostana* along (GM) | *P. quinquefoliu* alone (PQ) | *G. mangostana* and *P. quinquefoliu* (GM + PQ) |
| --- | --- | --- | --- |
| 1/2000 | 5 μg/ml | 10 μg/ml | 5 μg/ml + 10 μg/ml |
| 1/1000 | 10 μg/ml | 20 μg/ml | 10 μg/ml + 20 μg/ml |
| 1/500 | 20 μg/ml | 40 μg/ml | 20 μg/ml + 40 μg/ml |
| 1/250 | 40 μg/ml | 80 μg/ml | 40 μg/ml + 80 μg/ml |

Figure 1A:
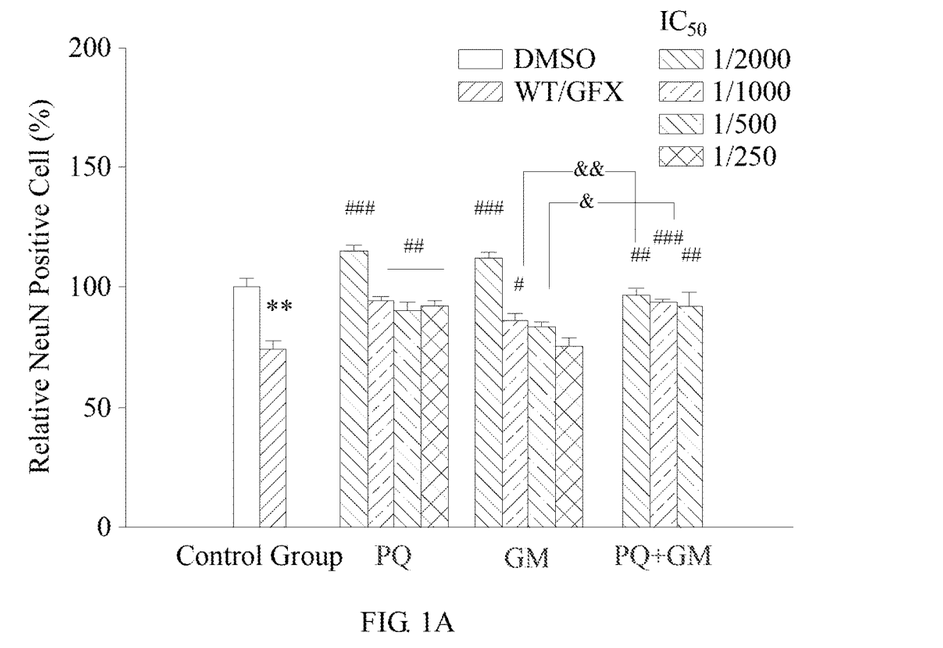
FIG. 1A shows the relative NeuN protein positive cells, which can be used to determine the survival rate of the neural cells.
Figure 1B:
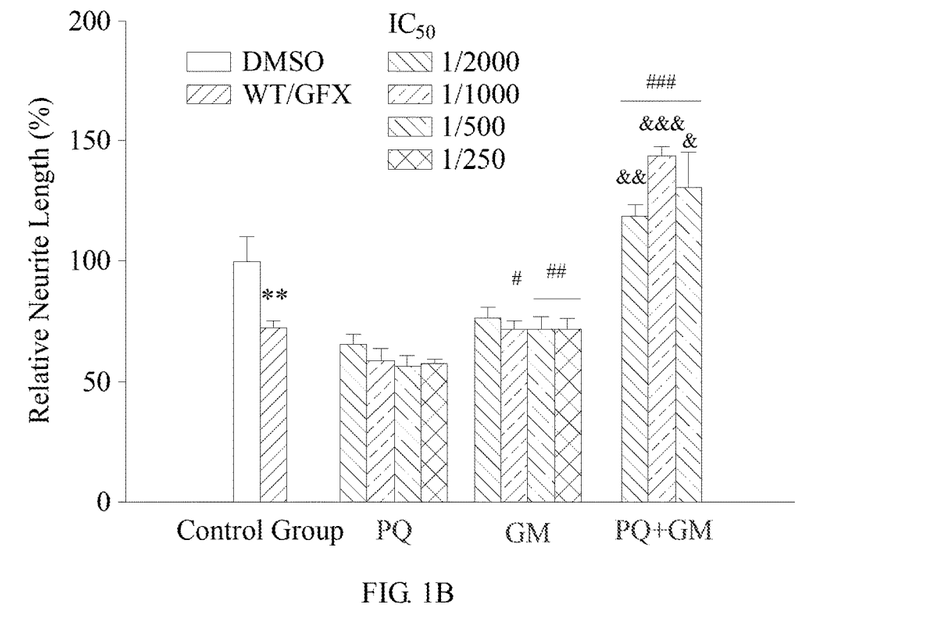

The results of the experiment are shown in FIGS. 1A and 1B. The percentage of relative NeuN positive cells in FIG. 1A shows that the survival rate of the neurons is boosted, regardless of the amount of *G. mangostana* (GM) or *P. quinquefoliu* (PQ) applied, i.e. $IC_{50}/2000$, $IC_{50}/1000$, $IC_{50}/500$ or $IC_{50}/250$, wherein $IC_{50}$ stands for the corresponding half maximal inhibitory concentration of *G. mangostana* (GM) or *P. quinquefoliu* (PQ). Besides, when *G. mangostana* is used in conjunction with *P. quinquefoliu* (GM+PQ), the survival rate of the neurons is boosted even more. (# and &, $p<0.05$; **, ## and &&, $p<0.01$; ###, $p<0.001$). FIG. 1B shows the neurite lengths of the primary hippocampal neurons of the laboratory mice after treatment. The results show that the neurite length is reduced when either *G. mangostana* (GM) or *P. quinquefoliu* (PQ) is used, and when *G. mangostana* is used in conjunction with *P. quinquefoliu*, (GM+PQ) the neurite length is increased. (# and &, $p<0.05$; **, ## and &&, $p<0.01$; ### and &&&, $p<0.001$). i.e., the combination of *G. mangostana* and *P. quinquefoliu* (GM+PQ) is more effective than *G. mangostana* (GM) or *P. quinquefoliu* (PQ) alone. Therefore, the present invention that combines both *G. mangostana* and *P. quinquefoliu* has enhanced efficacy in restoring AD-stricken cells.

In Vivo Experiment

From the aforementioned in vitro experiment, the inventor had gained the preliminary results, which show that the application of the combination of *G. mangostana* and *P. quinquefoliu* to the AD cells in growth medium is effective in restoring the neurons therein. Therefore, the inventor intended to further apply the combination to the mouse model, to test whether the composition of the present invention is capable of improving the learning ability and memory of test subjects with AD.

Figure 2A:
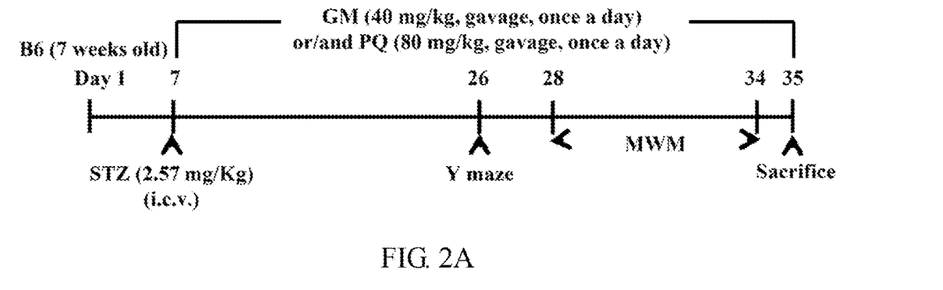
FIG. 2A is the timing diagram of the animal experiment.
Figure 2B:
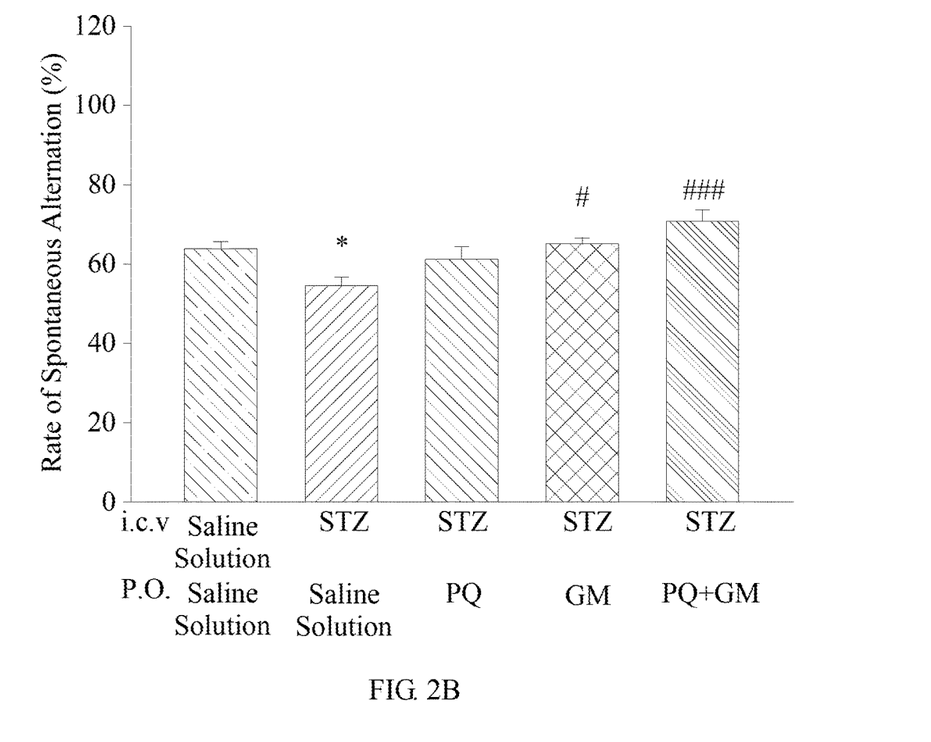

FIGS. 2A and 2B illustrate the procedure of the animal testing and the experiment results for Y maze test. FIG. 2A is the timing diagram of the animal experiment. The inventor let the C57B/6 (B6) mice purchased from the animal center adapt to the environment of the experiment for 6 days. Then, on day 7, one side (left side) of the cerebral lateral ventricle of the mouse was injected with streptozotocin (STZ), so as to establish animal model with sporadic AD, whereas the left cerebral lateral ventricle of the mice in the control group was injected with saline solution. Subsequently, the mice were fed per os (P.O.) with 40 mg (anhydrous) of *G. mangostana* for every kilogram net weight of mouse (GM, 40 mg/kg), 80 mg of *P. quinquefoliu* for every kilogram net weight of mouse (PQ, 80 mg/kg), or *G. mangostana* plus *P. quinquefoliu*, (GM+PQ, GM: 40 mg/kg; PQ: 80 mg/kg), for a total of four weeks. Next, on day 26, Y maze analysis was conducted, and on day 28-34, Morris water maze (MWM) analysis was conducted. Finally, the mice were sacrificed on day 35.

Proceeding to FIG. 2B, the reduced spontaneous alternation rate of the mice shows that the mice suffer from short term memory loss because of the sporadic AD caused by the intracerebroventricular injection of STZ thereto. However, the administration of G. mangostana and/or P. quinquefoliu is able to restore short term memory of the mice. In particular, when the combination of G. mangostana and P. quinquefoliu is administered (the bar PQ+GM), the short term memory of the mice is restored dramatically. (* and #, p<0.05; ##, p<0.01).

Figure 3A:
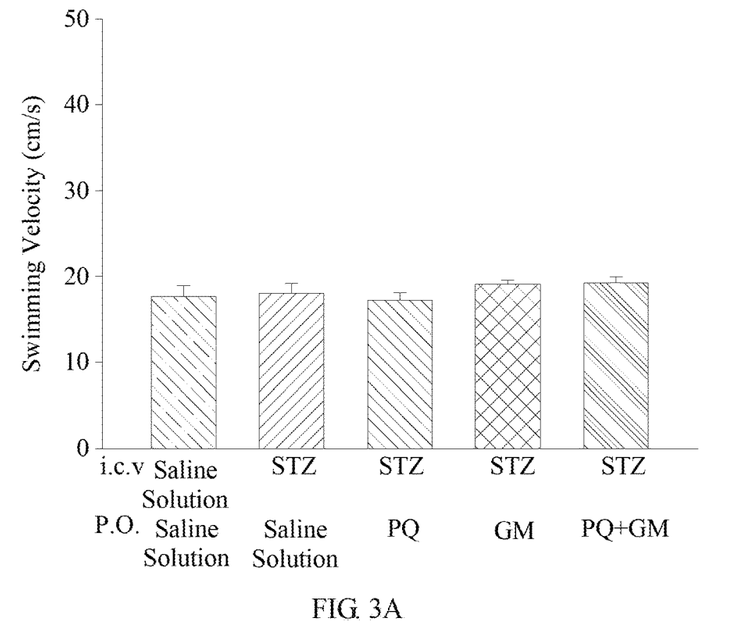
FIG. 3A shows no difference in swimming velocity of these groups of the laboratory mice on day 33.
Figure 3B:
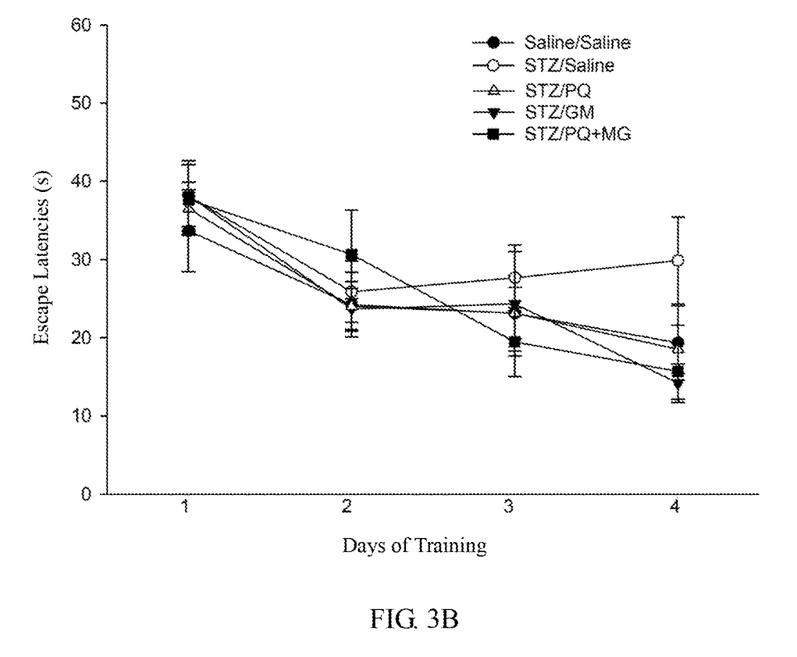
FIG. 3B presents the learning curve for training trial that lasts for 4 days (on days 29-32): normal mice (●, $F_{(3, 39)}=5.754$; $p=0.003$); mice having intracerebroventricular (I.C.V) injection with STZ (○, $F_{(3, 39)}=1.478$; $p=0.237$); mice administered with *P. quinquefolius* alone (PQ) (△, $F_{(3, 43)}=4.716$; $p=0.007$); mice administered with *G. mangostana* alone (GM) (▲, $F_{(3, 31)}=6.619$; $p=0.002$); or mice administered with both *G. mangostana* and *P. quinquefolius* (PQ+GM) (■, $F_{(3, 31)}=7.090$; $p=0.001$).
Figure 3C:
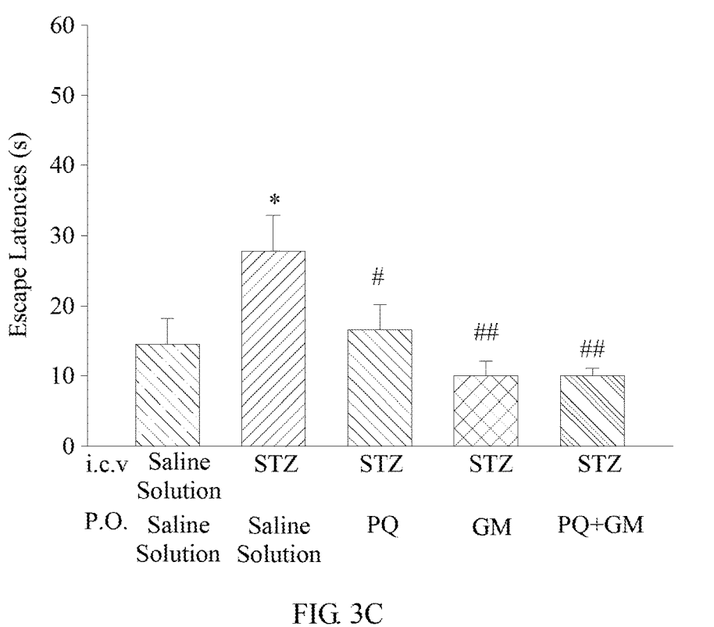
Figure 3D:
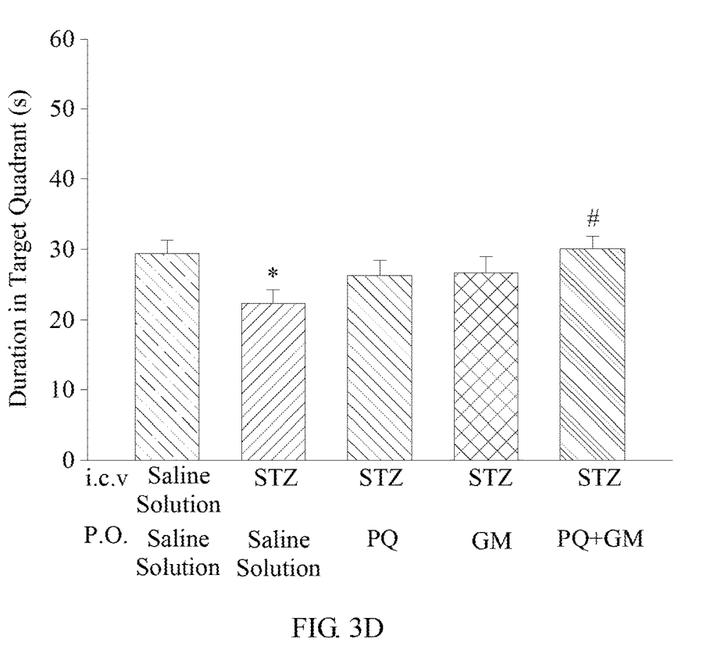

After this, MWM experiment is conducted. A pool was filled with white toxic-free poster paint, such that the non-transparent liquid therein can hide the platform, and the mice were unable to locate the platform in advance. The mouse was placed in the pool so that the mouse will search for the platform that was submerged in the liquid and fixed at certain quadrant of the pool. FIGS. 3A to 3D illustrate the analyzed results of the MWM experiment. FIG. 3A shows the analysis of the laboratory mice swimming velocity. The results indicate that the swimming velocities of the mice from each group are relatively identical, so there is no difference in their initial physical strengths. FIG. 3B depicts the learning curve for training trial that lasts for 4 days (on days 29-32). FIG. 3B shows that, when the brains of the normal mice are injected with saline solution, the learning ability thereof is not affected, as illustrated by the effective learning curve (●). However, when the brains of the mice are injected with STZ, the learning ability thereof drops, as illustrated by the ineffective learning curve (○). On the other hand, when either P. quinquefoliu (PQ) (△) or G. mangostana (GM) (▼) is administered to the mice, and when the combination of both G. mangostana and P. quinquefoliu (PQ+GM) (■) is administered to the mice, the effective learning curve is restored. Subsequently, after the training trial, a testing trial to evaluate the spatial learning of mice was conducted on day 33. FIG. 3C shows the result of the testing trial, compared to the control mice (injected with saline solution), the time to find the platform (escape latency) was increased in mice with STZ injection, indicating the learning ability was deteriorated in the sporadic AD mouse model. The learning ability was restored when the mice treated with G. mangostana and/or P. quinquefoliu. (* and #, p<0.05; ##, p<0.01). Finally, the long term memory of the mice is assessed on day 34 with the platform removed from the pool. It is shown in FIG. 3D, in contrast to normal mice (injected with saline solution), the long term memory of the mice having intracerebroventricular injection with STZ is substantially impaired. Whereas, when the combination of G. mangostana and P. quinquefoliu (GM+PQ) is administered to the mice, the duration of the mice staying in the quadrant where the platform once was has increased. This means that, the long term memory of the mouse inflicted with AD can be restored by administering the combination of G. mangostana and P. quinquefoliu thereto.

The inventor subsequently administered the mice per os using G. mangostana and P. quinquefoliu in certain range of doses and certain weight ratio. The amount of G. mangostana administered during the experiment equals to 40-320 mg per kilogram bodyweight of the mouse, whereas the amount of P. quinquefoliu administered during the experiment equals to 80-640 mg per kilogram bodyweight of the mouse. The details of the combination are listed in Table 3 below. The mice were administered per os with G. mangostana and/or P. quinquefoliu for a total of 4 weeks, and the memory and, learning ability test aforementioned was repeated. It is discovered that, when the combination of G. mangostana and P. quinquefoliu is administered to the mice suffering from AD, the impaired memory of the mice is restored. The details of the experiment procedure are similar to those disclosed in the context above, thus unnecessary details are omitted.

TABLE 3

The Doses of G. mangostana and P. quinquefolius Administered in the Embodiments of Present Invention

| | Weight of Each Ingredient in G. mangostana composition (Per Kilogram Bodyweight of Mouse) | | |
|---|---|---|---|
| Embodiments | G. mangostana (GM) | P. quinquefoliu (PQ) | G. mangostana:P. quinquefoliu (GM:PQ) |
| 1 | 40 | 80 | 1:2 |
| 2 | 80 | 160 | 1:2 |
| 3 | 240 | 480 | 1:2 |
| 4 | 320 | 640 | 1:2 |
| 5 | 320 | 80 | 4:1 |
| 6 | 80 | 80 | 1:1 |
| 7 | 40 | 640 | 1:16 |

When the G. mangostana composition of the present invention is to be administered to a human body, doses herein have to be converted to the optimal doses that can be administered to the human body based on the difference in metabolism rate between human and mouse. Therefore, for the G. mangostana composition of the present invention, the original doses administered to mouse are divided by 9, in order to determine the range of doses suitable for the human body. Therefore, the doses of G. mangostana for the human body range from 4.4 to 35.5 mg per kilogram bodyweight of human, whereas the doses of P. quinquefoliu for the human body range from 8.9 to 71 mg per kilogram bodyweight of human body.

In conclusion, after performing in vitro and in vivo tests, the G. mangostana composition of the present invention, i.e. the combination of G. mangostana and P. quinquefoliu, is found to be capable of reducing the neuronal cell death and increasing the neurite length of the patients with AD, as well as improving the short term memory and the long term memory of the test subjects, in addition to enhancing the learning ability of the test subjects.

The present invention has been described with some preferred embodiments thereof and it is understood that many changes and modifications in the described embodiments can be carried out without departing from the scope and the spirit of the invention that is intended to be limited only by the appended claims.

What is claimed is:

1. A tablet consisting essentially of a petroleum ether, methyl benzene or propanol extract of *Garcinia mangostana* and *Panax quinquefolius*.

* * * * *